(12) United States Patent
McGuinn et al.

(10) Patent No.: US 10,925,729 B2
(45) Date of Patent: Feb. 23, 2021

(54) STENTED PROSTHESIS DELIVERY DEVICE HAVING TORQUE SHAFT

(71) Applicant: Medtronic Vascular, Inc., Santa Rosa, CA (US)

(72) Inventors: Alan McGuinn, Galway (IE); Luke Lehmann, Newport Beach, CA (US); Wayne Falk, Minneapolis, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 175 days.

(21) Appl. No.: 16/037,139

(22) Filed: Jul. 17, 2018

(65) Prior Publication Data

US 2019/0015206 A1     Jan. 17, 2019

Related U.S. Application Data

(60) Provisional application No. 62/533,167, filed on Jul. 17, 2017.

(51) Int. Cl.
| | |
|---|---|
| *A61F 2/24* | (2006.01) |
| *A61F 2/95* | (2013.01) |
| *A61F 2/966* | (2013.01) |

(52) U.S. Cl.
CPC .............. *A61F 2/2439* (2013.01); *A61F 2/95* (2013.01); *A61F 2/2418* (2013.01); *A61F 2/9517* (2020.05); *A61F 2/9522* (2020.05); *A61F 2002/9511* (2013.01); *A61F 2002/9665* (2013.01)

(58) Field of Classification Search
CPC .. A61F 2/2427–2439; A61F 2002/9511; A61F 2/95
See application file for complete search history.

(56) References Cited

U.S. PATENT DOCUMENTS

| 10,786,351 B2* | 9/2020 | Christianson ........... A61F 2/246 |
| 2010/0049293 A1* | 2/2010 | Zukowski ................. A61F 2/07 |
| | | 623/1.11 |
| 2010/0049294 A1* | 2/2010 | Zukowski ............... A61F 2/954 |
| | | 623/1.11 |

(Continued)

OTHER PUBLICATIONS

PCT International Search Report and Written Opinion dated Oct. 2, 2018 from PCT counterpart PCT/US2018/042420.

*Primary Examiner* — Gregory A Anderson
*Assistant Examiner* — Brigid K Byrd
(74) *Attorney, Agent, or Firm* — Dicke, Billig & Czaja, PLLC

(57) ABSTRACT

Delivery devices for delivering a stented prosthesis to a target site are disclosed. Certain disclosed delivery devices include a handle assembly including an actuator, a shaft assembly interconnected to the handle assembly, and are configured to releasably retain the stented prosthesis to the delivery device with at least one elongate tension member. The delivery devices further include a torque shaft that is configured to apply and adjust the amount of tension in the each tension member. For example, the torque shaft can be configured to wind and unwind each elongate tension member around the torque shaft to correspondingly compress and expand the stented prosthesis. The torque shaft can be controlled with an actuator provided in the handle assembly, for example. In some embodiments, the actuator is further configured to axially move the torque shaft.

19 Claims, 7 Drawing Sheets

(56) References Cited

U.S. PATENT DOCUMENTS

| | | | |
|---|---|---|---|
| 2013/0245752 A1* | 9/2013 | Goetz | A61F 2/95 623/2.11 |
| 2014/0172069 A1* | 6/2014 | Roeder | A61F 2/95 623/1.12 |
| 2014/0330368 A1 | 11/2014 | Gloss et al. | |
| 2016/0250051 A1 | 9/2016 | Lim et al. | |
| 2017/0095331 A1* | 4/2017 | Spenser | A61F 2/2436 |

* cited by examiner

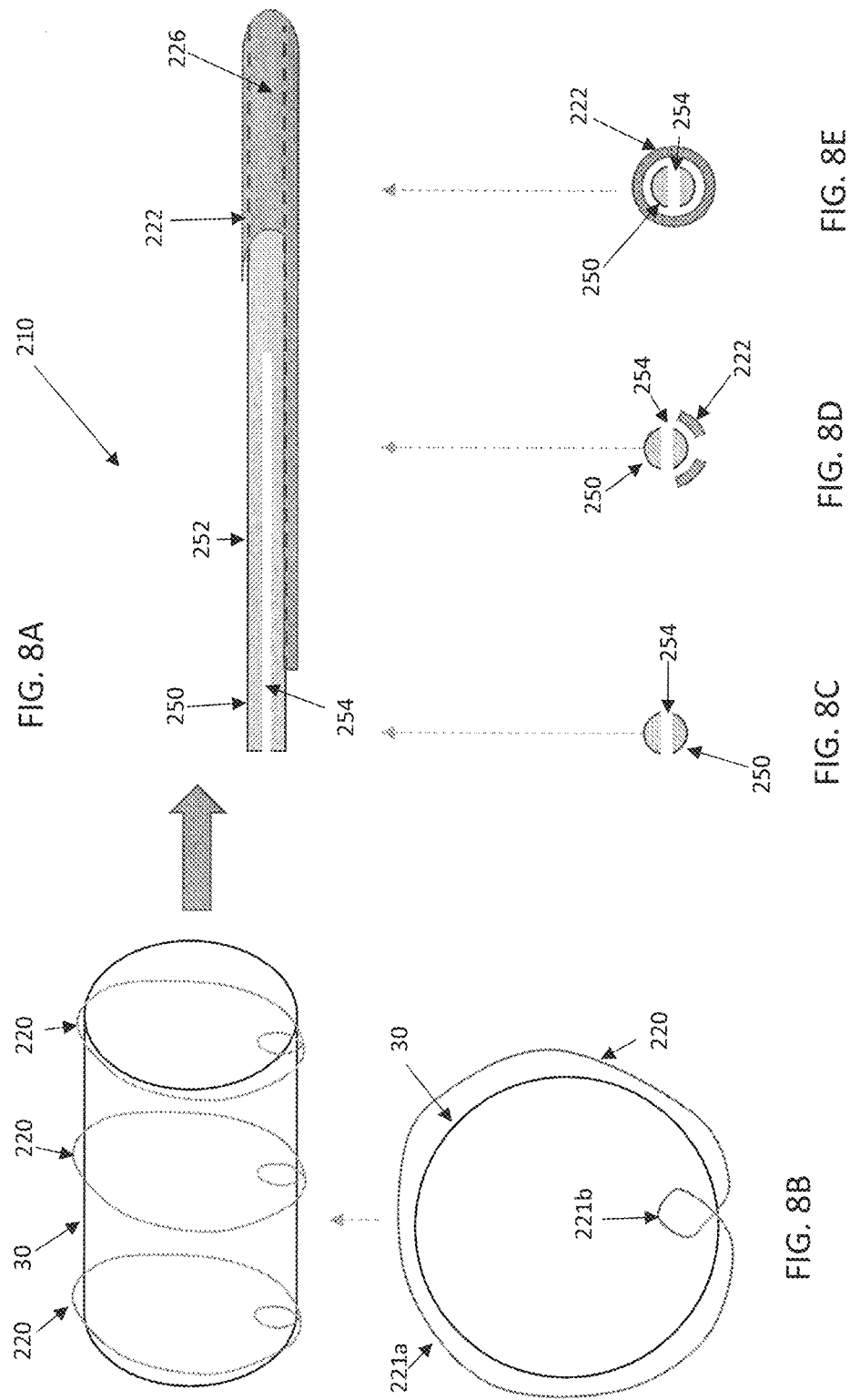

FIG. 9A
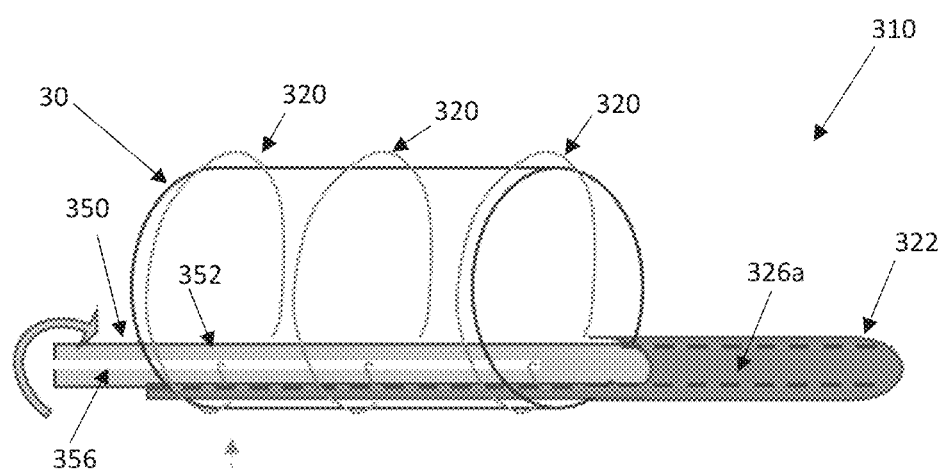
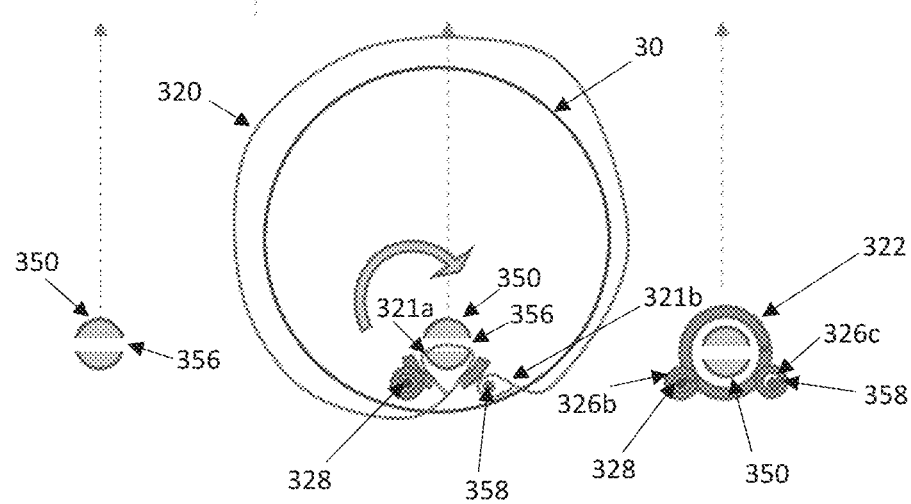
FIG. 9B    FIG. 9C    FIG. 9D

US 10,925,729 B2

STENTED PROSTHESIS DELIVERY DEVICE HAVING TORQUE SHAFT

CROSS-REFERENCE TO RELATED APPLICATIONS

This Non-Provisional Patent Application claims the benefit of the filing date of U.S. Provisional Patent Application Ser. No. 62/533,167, filed Jul. 17, 2017, the entire teachings of which are incorporated herein by reference.

BACKGROUND

This disclosure relates to delivery devices and tensioning devices to apply and adjust tension in at least one elongate tension member retaining a stented prosthesis to the delivery device.

A human heart includes four heart valves that determine the pathway of blood flow through the heart: the mitral valve, the tricuspid valve, the aortic valve, and the pulmonary valve. The mitral and tricuspid valves are atrio-ventricular valves, which are between the atria and the ventricles, while the aortic and pulmonary valves are semilunar valves, which are between the ventricles and the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Diseased or otherwise deficient heart valves can be repaired or replaced using a variety of different types of heart valve surgeries. One conventional technique involves an open-heart surgical approach that is conducted under general anesthesia, during which the heart is stopped and blood flow is controlled by a heart-lung bypass machine.

More recently, minimally invasive approaches have been developed to facilitate catheter-based implantation of the valve prosthesis on the beating heart, intending to obviate the need for the use of classical sternotomy and cardiopulmonary bypass. In general terms, an expandable valve prosthesis is compressed about or within a catheter, inserted inside a body lumen of the patient, such as the femoral artery, and delivered to a desired location in the heart where the valve prosthesis is then deployed.

The disclosure presents improvements related to the above.

SUMMARY

Aspects of present disclosure relate to delivery devices for stented prosthesis loading, delivery and implantation. Such delivery devices can include an optional outer delivery sheath assembly, a shaft assembly and a handle assembly. The delivery devices provide a loaded delivery state in which the stented prosthesis is loaded and compressed over the shaft assembly. Compression of the stented prosthesis can be adjusted with one or more elongate tension members, e.g., sutures or the like, which extend around the stented prosthesis. The delivery device can be manipulated to adjust tension in the tension members to permit the stented prosthesis to compress, self-expand, and ultimately release from the shaft assembly. In some embodiments, the tension members extend from the stented prosthesis proximately to an actuation and release assembly, which can, for example, be provided proximate to the stented prosthesis or in the handle assembly. In some embodiments the tension members are withdrawn from the patient after deploying the stented prosthesis and in other embodiments, the tension members can remain with the stented prosthesis after deployment.

The delivery device can further include a torque shaft to maintain and adjust the compression of the stented prosthesis by adjusting a length of tension member wrapped around the stented prosthesis. In various embodiments, the torque shaft is arranged to reel in the tension members radially to spool the tension members around the torque shaft. The delivery device can also be configured, via the handle assembly or otherwise, to move the torque shaft axially as the tension members wind upon the torque shaft. In some embodiments, the torque shaft has a varied diameter to correspondingly vary the length of each tension member wound around the torque shaft along its length. Various disclosed embodiments eliminate the need for the tension members to extend to the handle assembly, which reduces the risk of tension member tangling, damage, failure and also potential assembly errors. Additional benefits of the disclosed embodiments are discussed below.

BRIEF DESCRIPTION OF THE DRAWINGS

FIG. 8A is a partial, schematic illustration of the stented prosthesis being loaded onto a distal end of an alternate delivery device with a plurality of elongate tension members.

FIG. 8B is a schematic end view of the stented prosthesis and tension members of FIG. 8A.

FIGS. 8C-8E are cross-sectional views of the delivery device of FIG. 8A at various locations along a length of the delivery device.

FIG. 9A is a partial, schematic illustration of the stented prosthesis loaded onto a distal end of yet another alternate delivery device.

FIGS. 9B-9D are cross-sectional views taken at various locations along FIG. 9A.

DETAILED DESCRIPTION

Specific embodiments of the present disclosure are now described with reference to the figures, wherein like reference numbers indicate identical or functionally similar elements.

Figure 1:
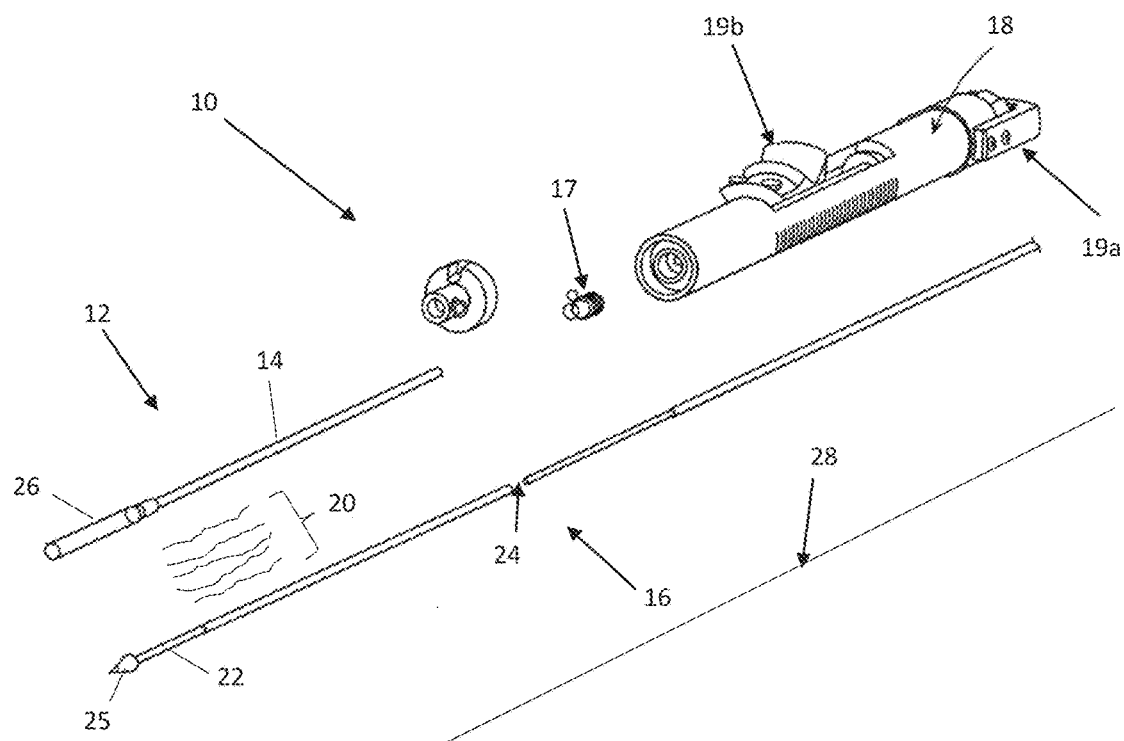
FIG. 1 is a perspective view of an example of a delivery device for delivering a stented prosthesis.
Figure 2:
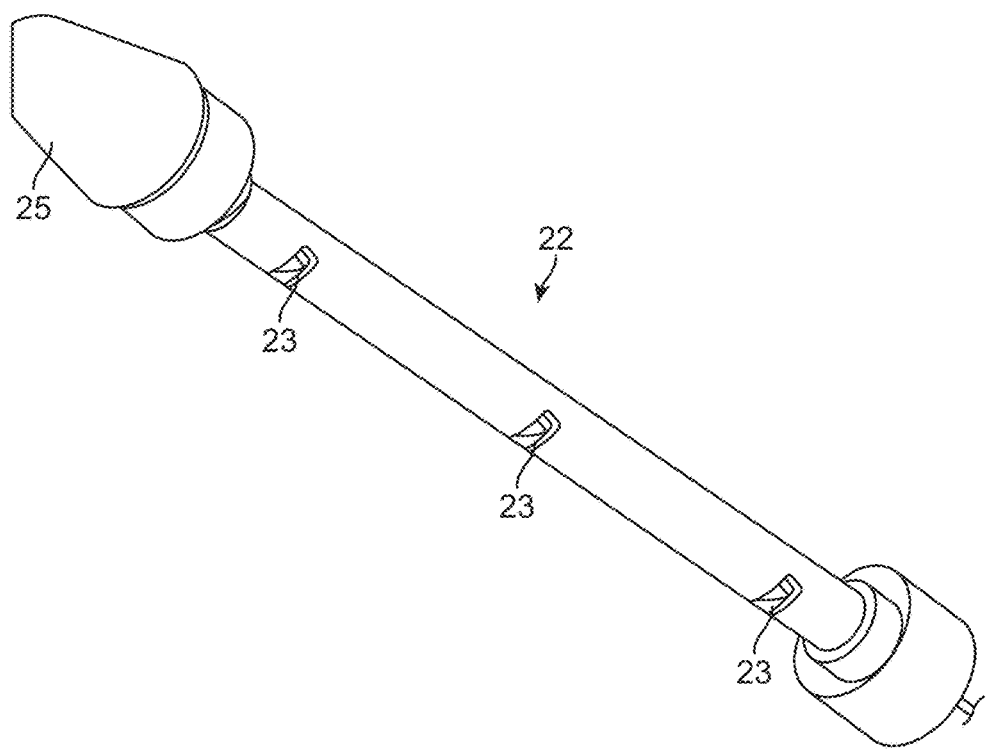
FIG. 2 is an enlarged view of a distal portion of the delivery device of FIG. 1.

As described below, aspects of the present disclosure relate to delivery devices utilizing one or more elongate tension members (e.g., sutures, cords, wires or filaments) to retain a stented prosthesis for delivery to a target site. By way of background, general components of one non-limiting example of a delivery device 10 with which some embodiments of the present disclosure are useful are illustrated in FIGS. 1-3B. The delivery device 10 is arranged and configured for percutaneously delivering a stented prosthesis. For example, the stented prosthesis can be a stented prosthetic heart valve 30 (schematically illustrated, hereinafter "stented prosthesis"). The delivery device 10 includes an optional outer sheath assembly 12 having an outer sheath 14, a shaft assembly 16 and a handle assembly 18. The shaft assembly 16 can define one or more continuous lumens 24 (referenced generally) sized to slidably receive an auxiliary component such as a guide wire 28 and/or one or more tension members 20. The tension members 20 can be considered part of the delivery device 10 in some embodiments or as part of the stented prosthesis 30 in other embodiments. The delivery device 10 provides a loaded, compressed arrangement (FIG. 3A) in which the stented prosthesis 30 is loaded over and is compressively retained on a spindle or distal portion 22 of the shaft assembly 16 by the tension members 20 and, in some embodiments, a valve retainer 17. The distal portion 22, as best shown in FIG. 2, can include a plurality of windows 23 through which one or more of the tension members 20 can be routed. In some embodiments, the distal portion 22 will include one respective window 23 for each tension member 20 provided. The distal portion 22 also includes a tip 25, which can be conically shaped or otherwise adapted to promote atraumatic contact with bodily tissue.

Figure 3A:
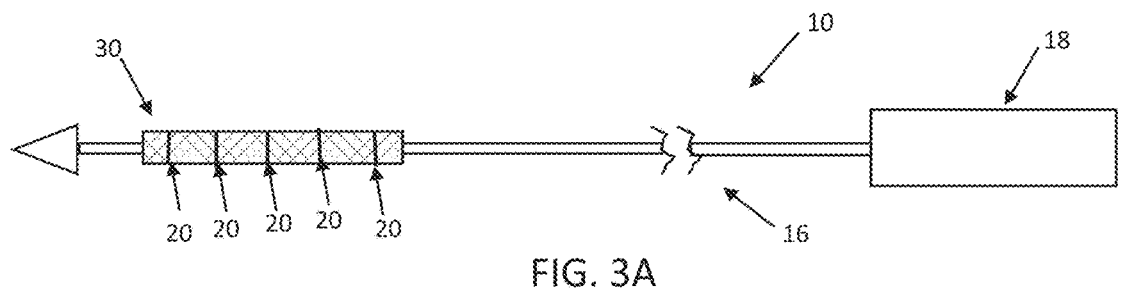
FIG. 3A is a schematic illustration of the delivery device of FIG. 1 having the stented prosthesis positioned over a shaft assembly of the delivery device in a compressed arrangement with a plurality of elongate tension members.
Figure 3B:
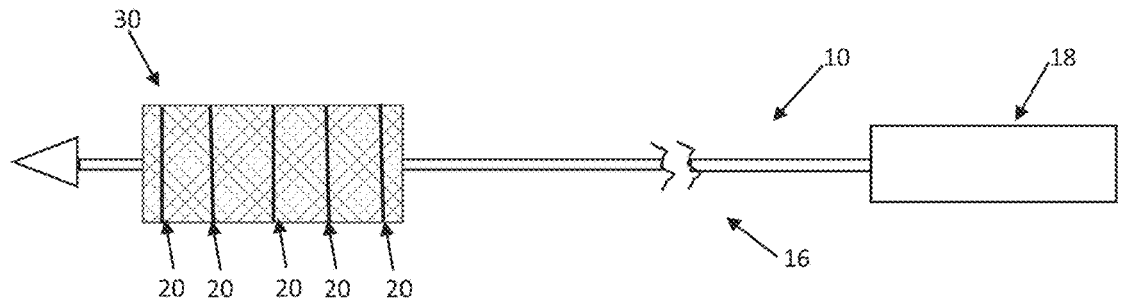
FIG. 3B is a schematic illustration of the delivery device of FIG. 2A having the stented prosthesis positioned over the shaft assembly of the delivery device in an expanded arrangement with the plurality of elongate tension members.

As is schematically illustrated in FIGS. 3A-3B, compression of the stented prosthesis 30 is adjustable by varying the tension in the one or more tension members 20. In this embodiment, the outer sheath 14 is interconnected to a capsule 26 that is selectively disposed over the compressed stented prosthesis 30 and assists in constraining the stented prosthesis 30. Once loaded, compressed and optionally sheathed by the capsule 26, the stented prosthesis 30 is delivered to the target site. When the stented prosthesis 30 is at the target site, the capsule 26 is withdrawn and tension in the tension members 20 is lessened or released to permit the stented prosthesis 30 to self-expand to an expanded arrangement, partially releasing and ultimately fully deploying the stented prosthesis 30 from the shaft assembly 16 (see, FIG. 3B). Movement of the outer sheath 14 and capsule 26 relative to the stented prosthesis 30 can be actuated by the handle assembly 18. Aspects of the present disclosure disclose ways to incorporate a torque shaft into a delivery device, such as the delivery device 10. As will be discussed in detail below, the disclosed delivery devices are arranged and configured to maintain and adjust the compression force that can be transferred to the stented prosthesis via the torque shaft and the one or more tension members.

As referred to herein, stented prostheses and stented prosthetic heart valves useful with the various devices and methods of the present disclosure may assume a wide variety of configurations, such as a bioprosthetic heart valve having tissue leaflets or a synthetic heart valve having polymeric, metallic or tissue-engineered leaflets, and can be specifically configured for replacing valves of the human heart. The stented prosthetic heart valves and other stented prostheses of the present disclosure may be self-expandable, balloon expandable and/or mechanically expandable or combinations thereof. In general terms, the stented prostheses of the present disclosure include a stent or stent frame having an internal lumen maintaining a valve structure (tissue or synthetic), with the stent frame having a normal, expanded condition or arrangement and collapsible to a compressed condition or arrangement for loading within the delivery device. For example, the stents or stent frames are support structures that comprise a number of struts or wire segments arranged relative to each other to provide a desired compressibility and strength to the stented prosthesis. The struts or wire segments are arranged such that they are capable of self-transitioning from, or being forced from, a compressed or collapsed arrangement to a normal, radially expanded arrangement. The struts or wire segments can be formed from a shape memory material, such as a nickel titanium alloy (e.g., Nitinol™). The stent frame can be laser-cut from a single piece of material, or can be assembled from a number of discrete components.

Figure 4A:
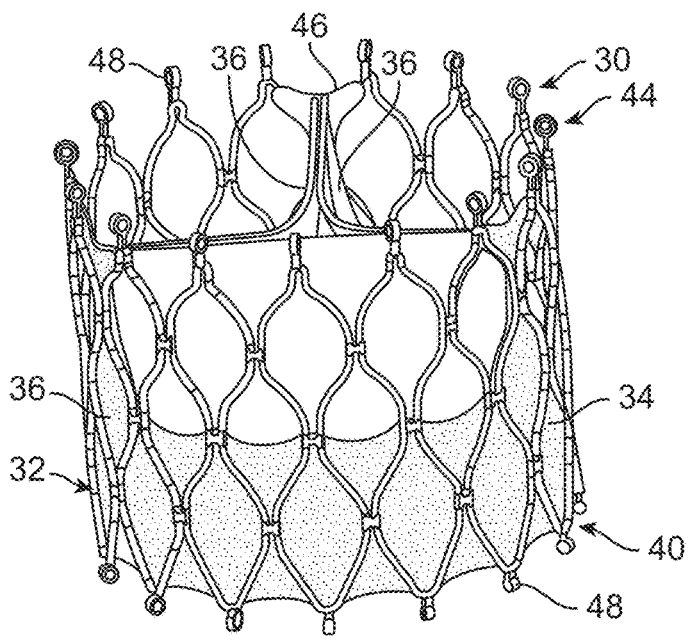
FIG. 4A is a perspective view of a stented prosthetic heart valve that can be used with the delivery devices disclosed herein shown in the expanded arrangement.
Figure 4B:
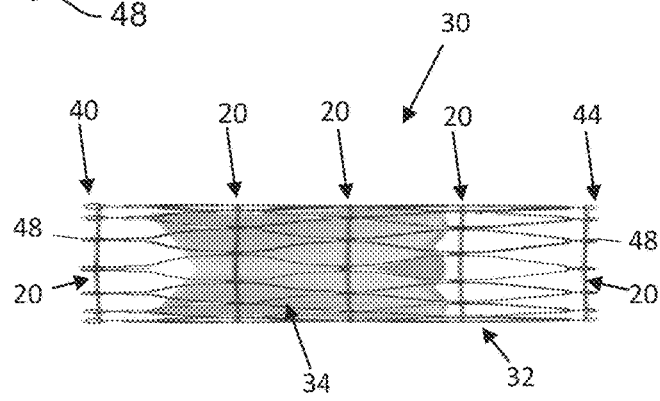
FIG. 4B is a front view of the stented prosthetic heart valve of FIG. 4A in the compressed arrangement.

The non-limiting example of the stented prosthesis 30 is illustrated in detail in FIGS. 4A-4B. As a point of reference, the stented prosthesis 30 is shown in a normal or expanded arrangement in the view of FIG. 4A and a compressed arrangement in the view of FIG. 4B. The stented prosthesis 30 includes a stent or stent frame 32 and a valve structure 34. The stent frame 32 can assume any of the forms mentioned above, and is generally constructed to be self or otherwise expandable from the compressed arrangement to the normal, expanded arrangement. As discussed above, compression of the stented prosthesis 30 can be achieved with one or more tension members 20.

If provided, the valve structure 34 of the stented prosthesis 30 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 34 can be formed, for example, from bovine, porcine, equine, ovine and/or other suitable animal tissues. In some embodiments, the valve structure 34 is formed, for example, from heart valve tissue, pericardium, and/or other suitable tissue. In some embodiments, the valve structure 34 can include or form one or more leaflets 36. For example, the valve structure 34 can be in the form of a tri-leaflet bovine pericardium valve, a bi-leaflet valve, or another suitable valve.

In some stented prosthesis constructions, such as that of FIGS. 4A-4B, the valve structure 34 can comprise two or three leaflets 36 that are fastened together at enlarged lateral end regions to form commissural joints, with the unattached edges forming coaptation edges of the valve structure 34. The leaflets 36 can be fastened to a skirt that in turn is attached to the stent frame 32. The stented prosthesis 30 includes a first end 40 and an opposing second end 44 of the stented prosthesis 30. As shown, the stent frame 32 can have a lattice or cell-like structure, and optionally forms or provides posts 46 corresponding with commissures of the valve structure 34 as well as features 48 (e.g., crowns, eyelets or other shapes) at the first and second ends 40, 44. If provided, the posts 46 are spaced equally around frame 32 (only one post 46 is clearly visible in FIG. 4A).

Figure 5:
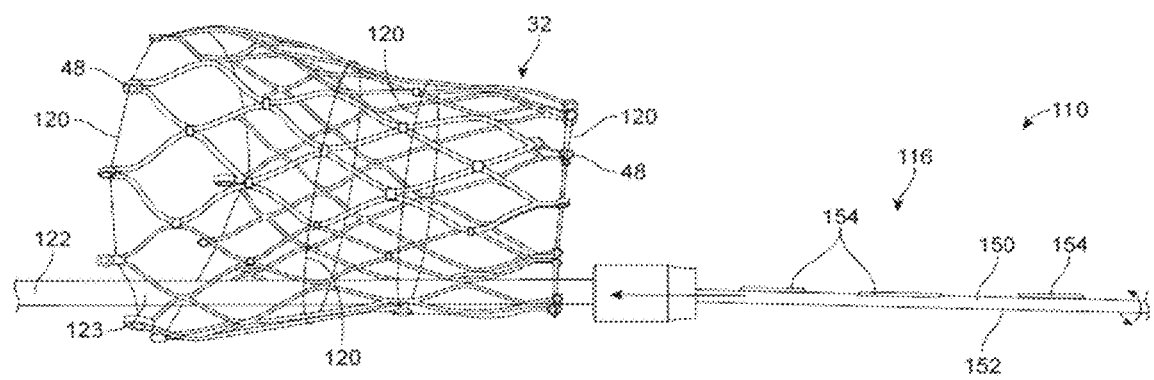
FIG. 5 is photograph of the stented prosthesis loaded over an alternate delivery device having a torque shaft (only a stent frame of the stented prosthesis and select components of the delivery device are shown).
Figure 6A:
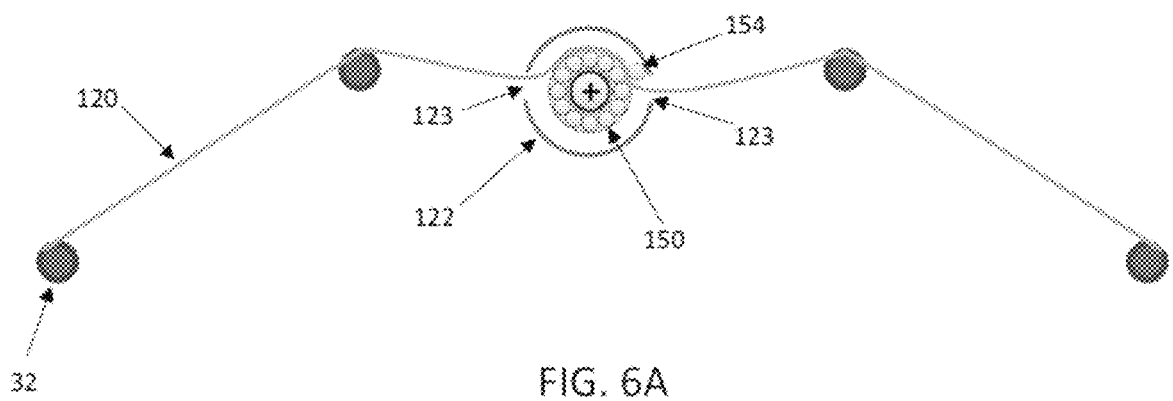
FIG. 6A is a partial, schematic cross-sectional view of the stent frame positioned loaded over the delivery device of FIG. 5 and retained thereon with at least one tension member (only one tension member is visible).
Figure 6B:
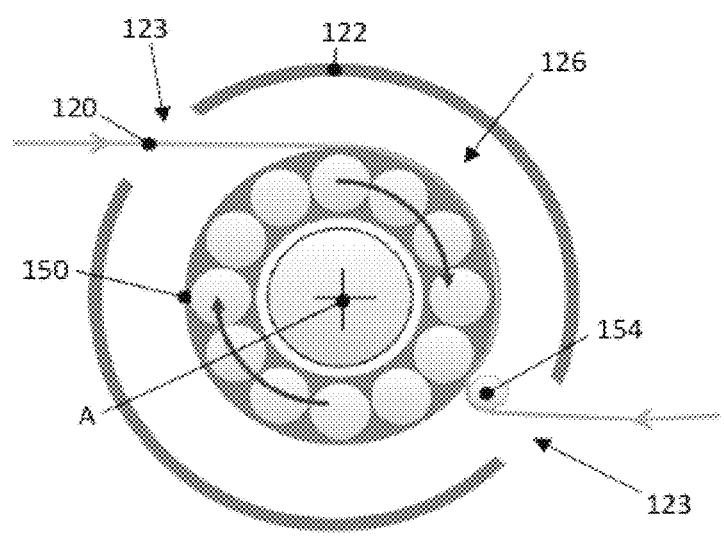
FIG. 6B is an enlarged, schematic illustration of the torque shaft of FIG. 6A engaging the tension member.
Figure 6C:
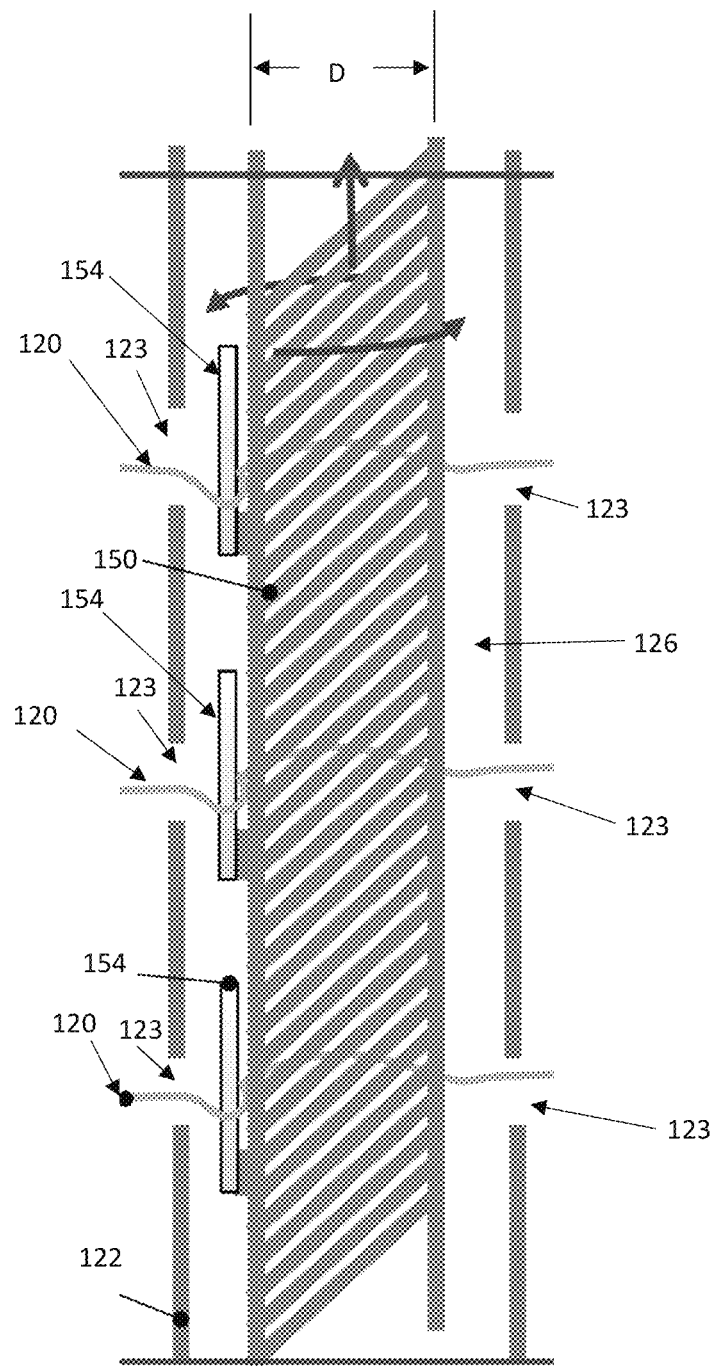
FIG. 6C is a cross-sectional schematic illustration of the torque shaft of FIGS. 6A-6B engaging a plurality of tension members.

Turning now to FIGS. 5-6C, which illustrate partial assembly of select components of an alternate delivery device 110 that includes a torque shaft 150 for adjusting the compression of a stented prosthesis positioned over a distal portion 122 of a shaft assembly 116 (only the stent frame 32 of the stented prosthesis is shown for ease of illustration). The delivery device 110 of FIGS. 5-6C can be largely similar to that of FIGS. 1-3B and differs only as explicitly stated. In this embodiment, the torque shaft 150 extends from a handle assembly 118, within a lumen 126 of the shaft assembly 116, and through the distal portion 122. The torque shaft 150 can include a shaft 152 having one or more barbs or pins 154. In some embodiments, the pins 154 are arranged to correspond in position and number to the windows or apertures 123 provided in the distal portion 122. After the torque shaft 150 is inserted at least partially within the distal portion 122, the expanded stent frame 32, including one or more tension members 120 of the type disclosed above, can be brought toward the windows 123 in the distal portion 122. The torque shaft 150 is then slid proximally so that the barbs 154 snag and engage one or more tension members 120. To further load the stent frame 32, the handle assembly 118 or the like actuates the torque shaft 150 so that the torque shaft 150 rotates about its longitudinal axis A and winds up the tension members 120 onto the shaft 152. To prevent the tension members 120 from sliding along a length of the stent frame 32, the tension members 120 can be secured to the stent frame 32 by threading the tension members 120 through features in the stent frame 32 (e.g., eyelets 48, which are generally referenced) or by threading the tension members 120 through suture loops or the like (not shown) attached to the stent frame 32.

Optionally, the torque shaft 150 can be provided having a varying diameter D to control and vary the length of each tension member 120 that will be would around the torque shaft 150 at various locations along the torque shaft 150. In one example, the diameter D can differ proximate each tension member 120. The diameter D can differ either via a taper or step-wise, as desired.

Figures 7A, 7B:
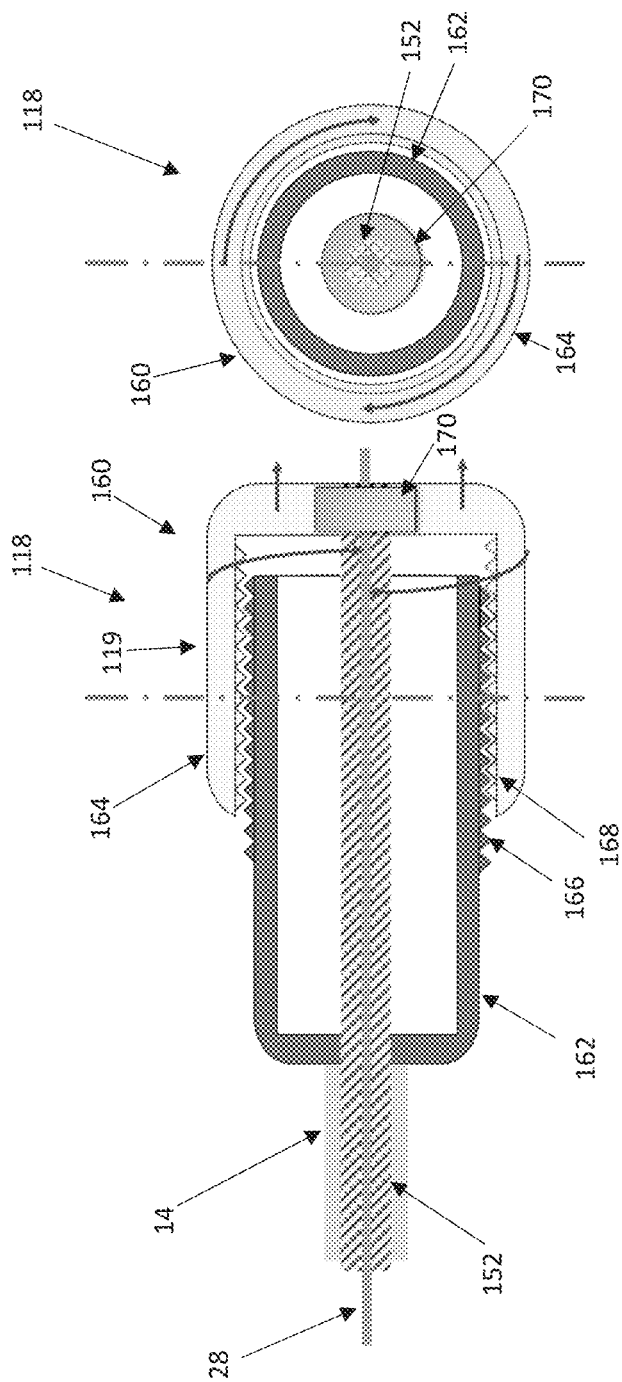
FIG. 7A is a cross-sectional schematic illustration of one embodiment of a handle assembly configured to rotate and axially adjust the position of the torque shaft of FIGS. 5-6C.
FIG. 7B is a cross-sectional schematic illustration of the handle assembly of FIG. 7A.

In some embodiments, the torque shaft 150 can be configured to slide axially as the tension members 120 are wound up onto the shaft 152 to avoid the tension members 120 from piling up on the shaft 152. FIGS. 7A-7B schematically illustrate a general handle assembly 118 that can be incorporated into a delivery device, such as the delivery device of FIG. 1. In this example embodiment, the handle assembly 118 includes a housing 160 having a first portion 162 including threads 166 to enable threadable connection to a second portion 164 having threads 168. A clamp 170 or the like fixedly secures the second portion 164 to the shaft 152. The first and second portions 162, 164 are arranged and configured to collectively function as an actuator 119 that can adjust the compression of the stented prosthesis (i.e. to compress or expand the stented prosthesis) via rotation of the shaft 152. In one example embodiment, the second portion 164 is rotated either clockwise or counterclockwise, respectively, with respect to the stationary, first portion 162. Due to the threaded interface between the first and second portions 162, 164, rotation of the second portion 164 not only rotates the shaft 152 to wind/unwind the tension members 120 but also causes the handle assembly 118 and the torque shaft 150 to move axially with respect to the rest of the delivery device 110. This axial movement allows the torque shaft 150 to move relative to the distal portion 122, which prevents tension member 120 overlap and bunching up as the tension members 120 are wound around the shaft 152 during compression of the stented prosthesis.

Once the compressed and loaded stented prosthesis 30 is delivered to a target site and is ready to be deployed, the torque shaft 150 can be rotated in the opposite direction to unwind the tension members 120 from the shaft 152. Once substantially all of the tension members 120 have been unwound, the tension members 120 will eventually disengage from the barbs 154. To release the tension members 120 from the stent frame 32, a cutting mechanism (not shown) can be provided to sever each of the tension members 120, as desired.

Referring now also to FIGS. 8A-8E, which illustrate select components of yet another embodiment delivery device 210 on which the stented prosthesis 30 or the like can be loaded. The delivery device 210 can be configured and function in ways described above with respect to other embodiments and differs only in ways explicitly stated. In this embodiment, the delivery device 210 includes a distal portion 222 having a lumen 226 in which a torque shaft 250 can be positioned. As with other disclosed embodiments, the torque shaft 250 can include a shaft 252 that extends to the handle assembly for actuation (not shown, e.g., the handle assembly 18 of FIG. 1 or the handle assembly 118 of FIGS. 7A-7B). The torque shaft 250 can include a slit 254 or be split to receive one or more tension members 220 positioned around the stented prosthesis 30. In such an embodiment, the tension members 220 can be configured, for example, to include a primary loop 221a generally circumscribing the stented prosthesis and a secondary loop 221b formed by twisting the respective tension member 220 for positioning within the slit 254 of the shaft 252. In this way, rotation of the torque shaft 250 in a first direction, via the actuator (not shown, e.g., any of the actuators disclosed above), will wind the tension members 220 around the torque shaft 250. Rotation of the torque shaft 250 in a second, opposite direction via the actuator will unwind the tension member(s) 220 from the torque shaft 250. In various embodiments, the stented prosthesis 30 can be released from the delivery device 210 by unwinding the tension members 220 from the torque shaft 250 and then proximally withdrawing the torque shaft 250 along with other components of the delivery device 210 so that the secondary loop 221b of each tension member 220 disengages from the slit 254. In such methods, the tension members 220 are left within the patient along with the deployed stented prosthesis 30.

FIGS. 9A-9D schematically illustrate select components of an alternate distal end of a delivery device 310 including a shaft assembly 316 having a distal portion 322 and a torque shaft 350. The components of FIGS. 9A-9C can be incorporated into a delivery device such as that of FIG. 1, for example, to function in similar ways except as explicitly stated. The torque shaft 350 can include a shaft 352 that is positioned within a lumen 326a extending through the shaft assembly 316 and the shaft 352 can extend to a handle assembly for actuation (not shown, e.g., the handle assembly 18 of FIG. 1 or the handle assembly 118 of FIGS. 7A-7B). The shaft assembly 316 can also include additional lumens 326b, 326c for optionally receiving a guide wire 328 and a release pin 358, respectively. As with prior disclosed embodiments, the stented prosthesis 30 can be loaded onto the distal portion 322 and compressively retained on the distal portion 322 with one or more tension members 320 (e.g., sutures, wires, cords, filaments). The torque shaft 350 can be positioned to extend distally past the distal portion 322 and can include a conical tip (not shown, see, e.g., the tip 25 of FIG. 1) or the torque shaft 350 can terminate proximal to a distalmost portion of the distal portion 322.

The shaft 352 can be configured to include slit 356 through which a first looped end 321a of each tension member 320 is positioned. The release pin 358 is threaded through a second looped end 321b of each tension member 320. Rotation of the torque shaft 350 within the distal portion 322, via the handle assembly or the like, subsequently winds each tension member 320 around the torque shaft 350 to compress the stented prosthesis 30. Rotation of the shaft 352 in the opposite direction correspondingly unwinds the tension members 320 from the torque shaft 350 allowing the stented prosthesis 30 to expand. Proximal retraction of the release pin 358 disengages each second looped end 321b from the release pin 358 such that the proximal withdrawal of the torque shaft 350 (along with the shaft assembly 316) will pull each tension member 320 around the stented prosthesis 30 and out of the patient, along with the rest of the delivery device.

Some of the disclosed embodiments are beneficial in that they lower the tension member removal force required through minimizing the length of tension member that needs to be pulled out from around the stented prosthesis. In addition, various disclosed embodiments omit tension member interactions or overlap, which provides more predictable and reliable compression and expansion of the stented prosthesis. Yet another benefit of various disclosed embodiments is that axial loads in the tension members are practically eliminated, which reduces inadvertent tension member steering of the delivery device and may also allow for the use of a distal portion that is made to be transparent or of a polymer. It is further believed that various disclosed embodiments reduce the forces applied at the windows in the distal portion and that the tension members make less angular transitions, which reduces wear of the tension members. It is further believed that various embodiments are easier to sterilize as the stented prosthesis is only connected to the tension members and the distal portion. Certain disclosed embodiments are suitable for use with a centrally positioned guide wire and, lumens within the shaft assembly can be reduced in number as compared to other alternate configurations in which the tension members extend from the stented prosthesis to the handle assembly. In addition, the many of the disclosed embodiments provide for symmetrical compression and expansion of the stented prosthesis.

Although the present disclosure has been described with reference to preferred embodiments, workers skilled in the art will recognize that changes can be made in form and detail without departing from the spirit and scope of the present disclosure.

What is claimed is:

1. A delivery device for delivering a stented prosthesis to a native heart valve, the delivery device comprising:
   a handle assembly;
   a shaft assembly including a lumen and a distal portion; wherein the shaft assembly is interconnected to the handle assembly and configured to releasably retain the stented prosthesis on the distal portion with an elongate tension member, the elongate tension member having a first looped end forming a first closed loop and a second looped end forming a second closed loop;
   an actuator;
   a torque shaft positioned at least partially within the lumen that can be rotated independently from the distal portion in first and second directions via the actuator to respectively wind and unwind the elongate tension member around the torque shaft; wherein the first closed loop is secured to the torque shaft; and
   a release pin slidably positioned within the distal portion, the release pin releasably engaged with the second closed loop.

2. The delivery device of claim 1, further comprising a plurality of elongate tension members; wherein each tension member winds around the torque shaft when the torque shaft rotates in the first direction and each of the plurality of tension members unwinds from the torque shaft when the torque shaft rotates in the second direction.

3. The delivery device of claim 1, wherein the actuator is part of the handle assembly.

4. The delivery device of claim 1, wherein the actuator is further configured to move the torque shaft axially as the actuator rotates the torque shaft.

5. The delivery device of claim 4, wherein the actuator rotates the torque shaft and moves the torque shaft axially simultaneously.

6. The delivery device of claim 1, wherein the torque shaft includes at least one barb along its length.

7. The delivery device of claim 6, wherein each barb has a rounded contact surface which engages the tension member.

8. The delivery device of claim 1, wherein the torque shaft has a varied diameter along its length.

9. The delivery device of claim 1, wherein the torque shaft extends distally past the distal portion.

10. The delivery device of claim 1, wherein the first closed loop is secured within a slit in the torque shaft.

11. The delivery device of claim 10, wherein the slit extends longitudinally within the torque shaft.

12. A method of loading a stented prosthesis to a delivery device, the method comprising:
   providing a stented prosthetic heart valve having a plurality of elongate tension members circumscribing the stented prosthetic heart valve; each elongate tension member having a first looped end forming a first closed loop and a second looped end forming a second closed loop;
   providing a delivery device including:
      a handle assembly;
      an actuator;
      a shaft assembly interconnected to the handle assembly;
      a torque shaft positioned at least partially within the shaft assembly, wherein the torque shaft can be rotated via the actuator; further wherein each first closed loop is secured to the torque shaft; and
      a release pin slidably positioned within the shaft assembly, the release pin releasably engaged with each second closed loop;
   positioning the stented prosthesis over the shaft assembly;
   engaging the torque shaft with the elongate tension members; and
   actuating the actuator as to rotate the torque shaft in a first direction to wind the plurality of elongate tension members around the torque shaft to compress the stented prosthetic heart valve over the shaft assembly.

13. The method of claim 12, further comprising the step of axially moving the torque shaft during the step of actuating.

14. The method of claim 13, wherein the step of axially moving the torque shaft is accomplished with the actuator.

15. The method of claim 14, wherein the actuator axially moves the torque shaft simultaneously when rotating the torque shaft.

16. The method of claim 12, further comprising the step of winding the torque shaft in a second direction to unwind the plurality of elongate tension members from the torque shaft.

17. The method of claim 16, wherein the step of engaging includes engaging a plurality of barbs of the torque shaft with the plurality of tension members.

18. The method of claim 12, wherein each first closed loop is secured within a slit in the torque shaft.

19. The method of claim 18, wherein the slit extends longitudinally within the torque shaft.

\* \* \* \* \*